United States Patent
Burgi et al.

(10) Patent No.: US 9,518,970 B2
(45) Date of Patent: Dec. 13, 2016

(54) METHOD FOR DETERMINING ANALYTE TYPE AND/OR CONCENTRATION WITH A DIFFUSION BASED METAL OXIDE GAS SENSOR

(71) Applicant: Sensirion AG, Stafa (CH)

(72) Inventors: Lukas Burgi, Zurich (CH); Frank Roeck, Wil (CH)

(73) Assignee: Sensirion AG, Stafa (CH)

( * ) Notice: Subject to any disclaimer, the term of this patent is extended or adjusted under 35 U.S.C. 154(b) by 99 days.

(21) Appl. No.: 14/161,192

(22) Filed: Jan. 22, 2014

(65) Prior Publication Data

US 2014/0212979 A1    Jul. 31, 2014

(30) Foreign Application Priority Data

Jan. 31, 2013    (EP) ..................................... 13405021

(51) Int. Cl.
   G01N 27/12    (2006.01)
   G01N 33/00    (2006.01)

(52) U.S. Cl.
   CPC ........ G01N 33/0016 (2013.01); G01N 27/124 (2013.01)

(58) Field of Classification Search
   CPC ................................................... G01N 27/12
   USPC ...... 422/83, 98; 436/34, 121, 128, 132, 139, 436/149, 151
   See application file for complete search history.

(56) References Cited

U.S. PATENT DOCUMENTS

| | | | |
|---|---|---|---|
| 4,244,918 A * | 1/1981 | Yasuda et al. ................... | 422/95 |
| 4,267,071 A * | 5/1981 | Jaffe ......................... | B01J 35/10 208/216 PP |
| 4,277,439 A * | 7/1981 | Yasuda et al. ................... | 422/94 |
| 4,399,684 A * | 8/1983 | Advani et al. ............... | 73/25.03 |
| 4,423,407 A * | 12/1983 | Zuckerman ....................... | 338/34 |
| 4,446,718 A * | 5/1984 | Bukowiecki et al. ....... | 73/31.06 |
| 4,453,151 A * | 6/1984 | Leary et al. ..................... | 338/34 |
| 4,562,723 A * | 1/1986 | Hubner ........................ | 73/31.07 |
| 4,567,475 A * | 1/1986 | Bukowiecki et al. ........ | 340/634 |
| 4,570,479 A * | 2/1986 | Sakurai ................ | G01N 27/417 204/412 |
| 4,627,269 A * | 12/1986 | Forster et al. ............... | 73/31.06 |

(Continued)

FOREIGN PATENT DOCUMENTS

| | | |
|---|---|---|
| CH | 691197 | 5/2001 |
| WO | 9519563 | 7/1995 |

OTHER PUBLICATIONS

Renkin, E. M., Journal of General Physiology 1954, 38, 225-243.*

(Continued)

*Primary Examiner* — Arlen Soderquist
(74) *Attorney, Agent, or Firm* — Cooper & Dunham LLP

(57) ABSTRACT

A measuring device is provided for determining the type and/or concentration a gaseous analyte from a set of analytes in a gaseous carrier. It comprises a housing having a passage to a cavity. A gas sensor with a heated metal-oxide sensing layer is arranged in the cavity. In order to gain a better understanding of the type of the analyte, diffusion effects are exploited by taking into account that the diffusion process through the passage as well as the catalytic reaction rate at the metal-oxide sensing layer depend on the type of the analyte. These material parameters can be determined by taking several measurements in a non-steady state of the concentration of the analyte within the cavity or while varying the reaction rate.

3 Claims, 2 Drawing Sheets

(56) References Cited

U.S. PATENT DOCUMENTS

| | | | |
|---|---|---|---|
| 4,706,493 A * | 11/1987 | Chang et al. | 73/31.06 |
| 4,847,783 A * | 7/1989 | Grace et al. | 702/24 |
| 4,896,143 A * | 1/1990 | Dolnick et al. | 340/634 |
| 4,953,387 A * | 9/1990 | Johnson et al. | 73/25.03 |
| 5,012,671 A * | 5/1991 | Yagawara et al. | 73/31.06 |
| 5,047,352 A * | 9/1991 | Stetter et al. | 436/181 |
| 5,055,270 A * | 10/1991 | Consadori et al. | 422/98 |
| 5,305,231 A * | 4/1994 | Coppler et al. | 702/24 |
| 5,397,442 A * | 3/1995 | Wachsman | G01N 27/4074 204/425 |
| 5,517,182 A * | 5/1996 | Yasunaga | 340/634 |
| 5,528,225 A * | 6/1996 | Sakai et al. | 340/632 |
| 5,573,728 A * | 11/1996 | Loesch et al. | 422/90 |
| 5,580,440 A * | 12/1996 | Ueno | G01N 27/419 123/510 |
| 5,624,641 A * | 4/1997 | Capetanopolous | G01N 27/4045 204/432 |
| 5,667,652 A * | 9/1997 | Liu | G01N 27/4074 204/412 |
| 5,823,044 A * | 10/1998 | Logothetis et al. | 73/23.2 |
| 5,831,145 A * | 11/1998 | Logothetis et al. | 73/23.2 |
| 5,858,739 A * | 1/1999 | Williams | 436/151 |
| 5,898,101 A * | 4/1999 | Lyle et al. | 73/23.2 |
| 6,055,840 A * | 5/2000 | Warburton | G01N 33/0016 73/1.04 |
| 6,055,849 A * | 5/2000 | Shioiri et al. | 73/31.06 |
| 6,095,681 A * | 8/2000 | Kunt et al. | 374/45 |
| 6,128,945 A * | 10/2000 | Shioiri et al. | 73/31.06 |
| 6,165,347 A * | 12/2000 | Warburton | G01N 27/4045 204/409 |
| 6,338,266 B1 * | 1/2002 | Warburton | G01N 27/4045 205/775 |
| 6,422,061 B1 * | 7/2002 | Sunshine et al. | 73/29.01 |
| 6,566,894 B2 * | 5/2003 | Rump | 324/681 |
| 8,972,204 B2 * | 3/2015 | Kellaway et al. | 702/24 |
| 2005/0053523 A1 * | 3/2005 | Brooke | 422/68.1 |
| 2007/0063858 A1 * | 3/2007 | Lee et al. | 340/632 |
| 2010/0098593 A1 * | 4/2010 | Trakhtenberg | G01N 27/127 422/98 |
| 2012/0272713 A1 * | 11/2012 | Kountotsis et al. | 73/23.3 |
| 2013/0062223 A1 * | 3/2013 | Rabbett | G01N 27/4074 205/793 |
| 2013/0081445 A1 | 4/2013 | De Coulon et al. | |
| 2013/0192338 A1 * | 8/2013 | Mayer et al. | 73/23.3 |
| 2014/0134053 A1 * | 5/2014 | Mayer et al. | 422/83 |
| 2014/0228698 A1 * | 8/2014 | Roeck et al. | 600/532 |
| 2014/0234172 A1 * | 8/2014 | Burgi et al. | 422/84 |

OTHER PUBLICATIONS

Warburton, P. R. et al, Analytical Chemistry 1998, 70, 998-1006.*
Satoshi Nakata et al., "Discrimination and Quantification of Flammable Gases with a Sn02 Sniffing Sensor", The Analyst, 2000, 125, pp. 517-522.
A. Lee et al. "Temperature Modulation in Semiconductor Gas Sensing", Sensors and Actuators B, 1999, No. 60, pp. 35-42.

* cited by examiner

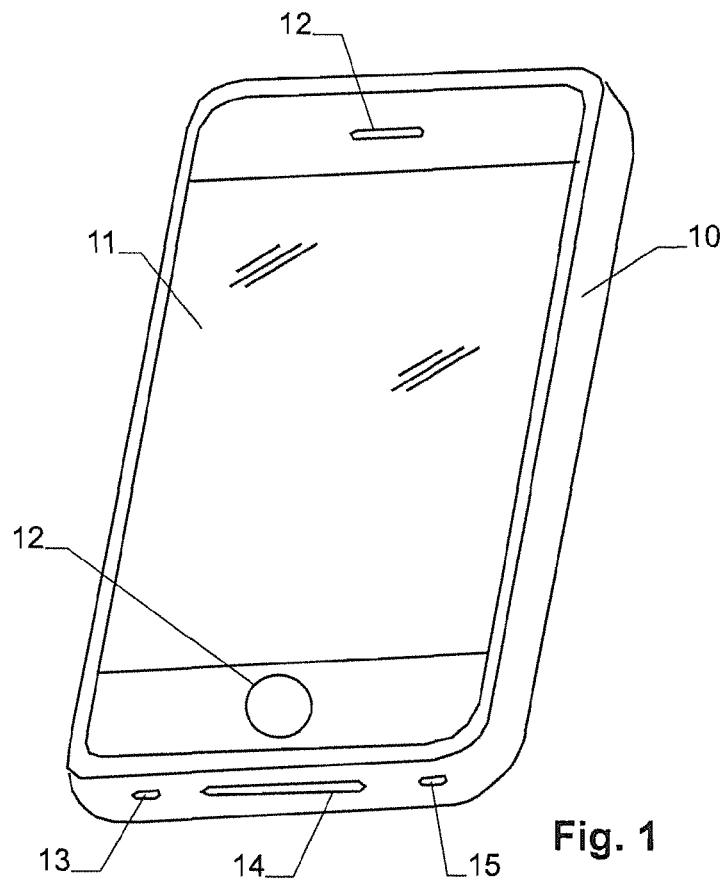
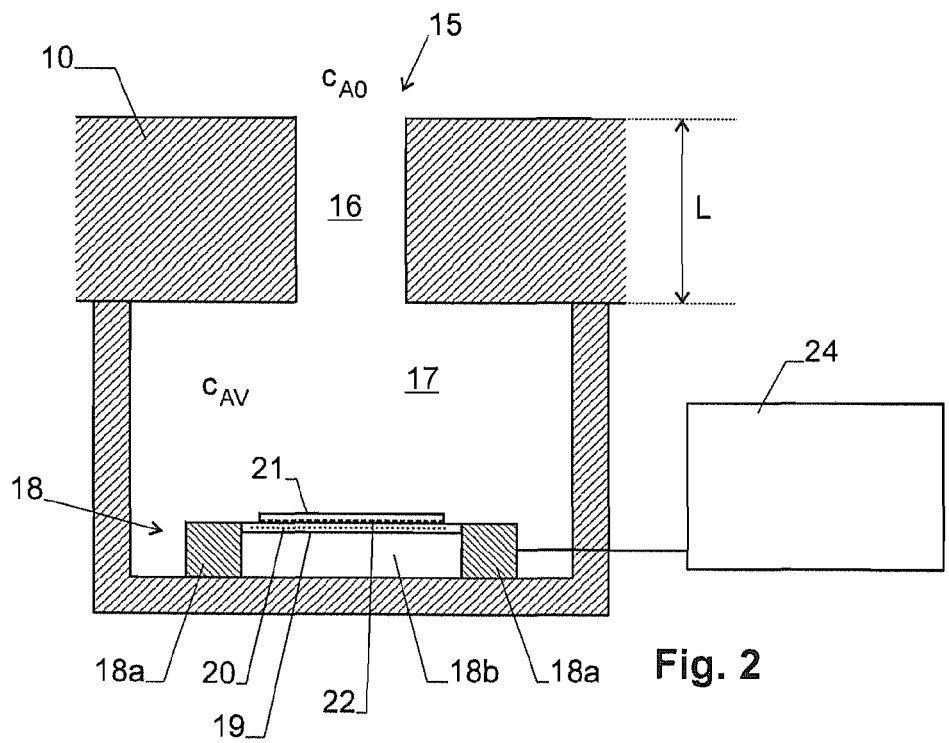
Fig. 1
Fig. 2

METHOD FOR DETERMINING ANALYTE TYPE AND/OR CONCENTRATION WITH A DIFFUSION BASED METAL OXIDE GAS SENSOR

FIELD OF THE INVENTION

The present invention relates to a method and device that allows to more precisely determine the concentration and/or type of a gaseous analyte from a set of analytes.

BACKGROUND OF THE INVENTION

Metal oxide gas sensors, such as tin oxide gas sensors, are suitable for detecting a variety of gases. One of the drawbacks of these sensors is their comparatively poor selectivity, i.e. one sensor usually responds to a variety of different gases (analytes), which makes it difficult to selectively measure one gas and/or to determine the nature of a gas that gives rise to a signal in the sensor.

SUMMARY OF THE INVENTION

Hence, the problem to be solved by the present invention is to provide a method and device that allow to more precisely determine the concentration and/or type of a gaseous analyte from a set of analytes (such as ethanol, CO, and others) in a gaseous carrier (such as air). Further, the invention relates to a measuring device adapted to carry out this method.

This problem is solved by the method and device according to the independent claims.

Accordingly, the method for identifying an analyte from a set of analytes comprises the steps of
  providing a measurement device having
    a housing
    a cavity within said housing,
    a metal-oxide gas sensor comprising a metal-oxide sensing layer and a heater for heating the sensing layer, and
    a passage extending between the cavity and the outside of the housing,
  heating the metal-oxide sensing layer, thereby generating a condition where said analyte is catalytically decomposed with a reaction rate k at said metal-oxide sensing layer,
  taking at least two measurements on said metal oxide sensing layer indicative of a concentration of said analyte, wherein the measurements are taken
    at different times during a phase where a concentration $c_{AV}$ of the analyte within the cavity is in a non-steady state and/or
    for different reaction rates k, and
  deriving at least one material parameter indicative of the analyte from said measurements.

As will be discussed in more detail below, this procedure exploits the fact that the diffusion of the analyte through the passage as well as the catalytic decomposition of the analyte at the metal-oxide sensing layer depend on the type of the analyte. By taking at least two measurements indicative of the electrical conductivity of the metal oxide sensing layer
  during a phase where the concentration $c_{AV}$ of the analyte within the cavity is in a non-steady state (e.g. after switching on the heater) and/or
  for different reaction rates k (e.g. induced by varying the temperature of the sensing layer)
a signal therefore can be obtained that depends on the type of the analyte and that allows to identify the same.

The material parameter "indicative of the analyte" can e.g. be an identifier of the analyte (such as "the analyte is ethanol"), or it can e.g. be an analyte-specific correction factor to be applied for subsequent concentration measurements.

The step of "taking at least two measurements on said metal oxide sensing layer indicative of a concentration of said analyte" can e.g. comprise taking at least two measurements indicative of the electrical conductivity of the metal oxide sensing layer.

Alternatively, the step of "taking at least two measurements on said metal oxide sensing layer indicative of a concentration of said analyte" can also comprise taking at least two measurements indicative of the heat of reaction of the decomposition of the analyte at the metal oxide layer. In this case, the measured value can e.g. be the change of temperature at the sensing layer due to an exothermal reaction of the analyte at the sensing layer.

The invention also relates to a sensor device comprising a control unit adapted to carry out this method.

The above and other aspects of the present invention together with further advantageous embodiments and applications of the invention are described in further details in the following description and figures.

BRIEF DESCRIPTION OF THE FIGURES

FIG. 1 is a perspective view of a portable electronic device with a gas sensor,

FIG. 2 is a sectional view of the device at the location of the gas sensor,

DETAILED DESCRIPTION

Device

Figure 3:
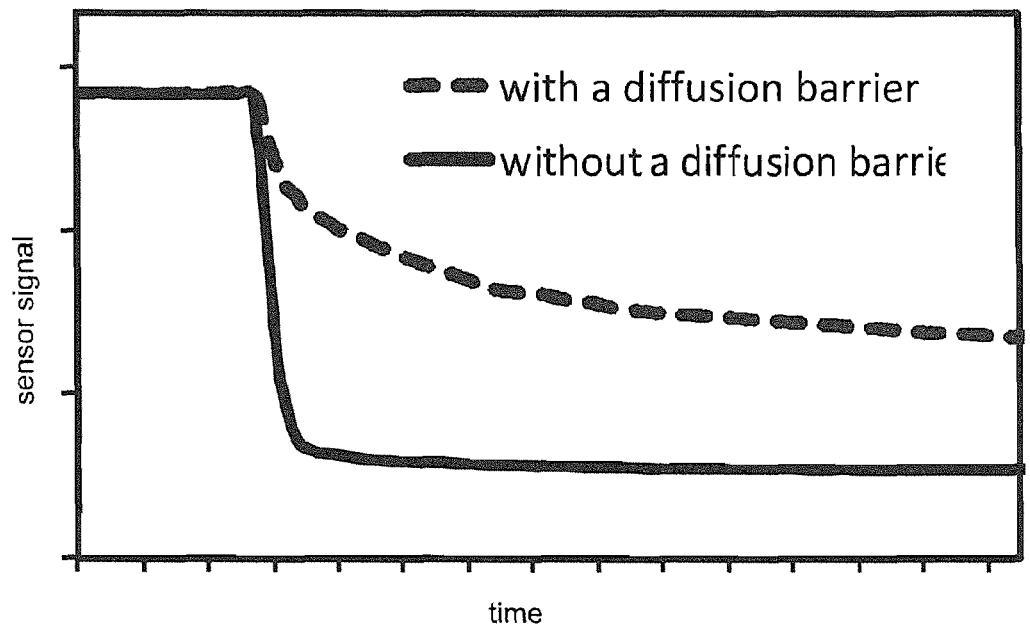
FIG. 3 shows the measured raw signal (resistance) of a device with and without diffusion barrier.

The measuring device of FIG. 1 is a portable electronic device such as a mobile phone. The housing 10 of the mobile phone includes a front side with a screen 11 and elements like buttons and loudspeaker 12 to let a user interact with the phone. Further openings 13, 14 are located at a lower side wall of the housing 10. It is well known to mount components like microphones and loudspeakers behind such openings. A further opening 15, which is e.g. also arranged on the lower side wall of housing 10, provides access to a gas sensor as described in the following.

FIG. 2 shows a sectional view through housing 10 at the location of the gas sensor.

As can be seen, opening 15 forms a passage 16 connected to a cavity 17 within housing 10. A gas sensor 18 is arranged within cavity 17. Gas sensor 18 is a MEMS-device and comprises a substrate 18a, such as a silicon substrate, with a hotplate arranged thereon. In the shown embodiment, this hotplate is formed by a membrane 19 extending over an opening 18b etched through substrate 18a.

A heater 20 is located in or on membrane 19, and a sensing layer 21 is applied to a surface of membrane 19. Interdigitated electrodes 22 are formed on the same surface and are in contact with sensing layer 21 in order to measure a conductance or resistance of the same.

The operation of gas sensor 18 is controlled by a control unit 24, which is adapted to carry out the steps of the method as described in the following.

Sensing layer 21 is a MOX (Metal Oxide) layer, such as a layer of Tin oxide. The MOX can also e.g. be tungsten oxide, gallium oxide, indium oxide, or zinc oxide, or a mixture of any of these materials, including Tin oxide.

Advantageously, sensing layer 21 is formed by particles that typically have a diameter of less than 1 µm and that are in contact with each other.

This type of gas sensor is e.g. described in WO 95/19563. It is operated by heating sensing layer 21 to a given temperature, which depends on the material of sensing layer 21 and is typically above 100° C., in particular above 300° C. for Tin oxide, whereupon a voltage is applied to the electrodes 22 and the resulting current is measured, thereby obtaining a signal indicative of the conductance or resistance of the sensing layer.

Device Kinetics:

The conductance of sensing layer 21 is a function of the composition of the gas surrounding the sensor, which is briefly described in the following.

The metal oxides used for sensors of this type are semiconductors with a certain degree of intrinsic conduction. In a nitrogen-oxygen atmosphere, oxygen is chemisorbed at the surface of the metal oxide. The chemisorbed oxygen binds a negative charge carrier, thereby generating a depleted surface layer and decreasing the material's conductance.

When a further gas (the "analyte") that reacts with the chemisorbed oxygen is brought into the neighborhood of sensing layer 21, the oxygen reacts with the analyte, the charge carriers bound by the oxygen atoms are released, and the electrical conductivity of the metal oxide changes, which can be used to detect the presence of the analyte.

For example, if CO is introduced, it reacts at the operating temperature of the sensor with the chemisorbed oxygen and forms $CO_2$. In more general terms, a catalytic reaction takes place at the heated sensing layer, which transforms an analyte A into a substance B.

Similar effects apply when the sensor is exposed to an oxidizing gas that e.g. binds to the surface of the metal oxide.

The present invention takes advantage of the kinetics of such a process in relation to the kinetics of diffusion processes in the measuring device in order to gain a better understanding of the nature of analyte A.

To start with, this is in the following described by reference to a simplified model.

Assuming that the concentration of the analyte in cavity 17 is $c_{AV}$, the number $N_A$ of molecules of the analyte in cavity 17 is $$N_A = c_{AV} \cdot V, \quad (1)$$

with V being the volume of cavity 17.

The number $N_A$ can change due to diffusion of molecules of the analyte through passage 16 and due to the catalytic decomposition of such molecules at the hot MOX sensing layer, i.e.

$$\frac{\partial N_A}{\partial t} = V \cdot \frac{\partial c_{AV}}{\partial t} = -S \cdot D \cdot \frac{c_{AV} - c_{A0}}{L} - k \cdot c_{AV}, \quad (2)$$

with S being the cross section area and L the length of passage 16, D being the diffusivity (or diffusion coefficient) of A in air and k being the reaction rate of analyte A into substance B.

Eq. (2) can be rewritten as $$\frac{\partial c_{AV}}{\partial t} = -\left(\frac{S \cdot D}{L \cdot V} + \frac{k}{V}\right) \cdot c_{AV} + \frac{S \cdot D}{L \cdot V} \cdot c_{A0} \quad (3)$$

This differential equation describes how concentration $c_{AV}$ (and therefore the measured signal) changes over time, taking into account the diffusion through passage 16 and the catalytic decomposition of A and the heated MOX sensor.

Assuming that, at a time t=0, concentration $c_{AV}$ has a value of $c_{AV}(0)$ and then the boundary conditions of the system change (e.g. the sensor heater is switched on), the change of $c_{AV}$ over time t can be calculated by integrating Eq. (3)

$$c_{AV}(t) = \left(c_{AV}(0) - \frac{c_{A0}}{1 + \frac{k \cdot L}{S \cdot D}}\right) \cdot e^{-t/\tau} + \frac{c_{A0}}{1 + \frac{k \cdot L}{S \cdot D}}, \quad (4)$$

with $$\tau = \frac{L \cdot V}{S \cdot D + L \cdot k} = \frac{L \cdot V}{S \cdot D} \cdot \frac{1}{1 + \frac{L \cdot k}{S \cdot D}} \quad (5)$$

In other words, the concentration $c_{AV}$ of the analyte at the location of the sensing layer reacts with a time constant τ according to Eq. (5) when the boundary conditions change.

A change of the boundary conditions may e.g. be due to a change of the concentration of the analyte $c_{A0}$ outside housing 10 at passage 16. For example, if the device is used for analyzing the breath of a person and the person blows onto the housing at time t=0, thereby increasing $c_{A0}(t)$ from zero to a value $c_{A0}$, the starting value $c_{AV}(0)$ is 0 and Eq. (5) can be written as $$c_{AV}(t) = \frac{c_{A0}}{1 + \frac{L \cdot k}{S \cdot D}} \cdot (1 - e^{-t/\tau}). \quad (6)$$

In other words, the concentration will rise with a the time constant τ to a final value $c_{A0}/(1+(L \cdot k)/(S \cdot D))$.

In an advantageous embodiment, the change in the boundary conditions may also be due to a change in the heating power. For example, the heater may be switched on at a given time t. In this case, the concentration $c_{AV}(t)$ is given by $$c_{AV}(t) = c_{A0} \cdot \left(\frac{1}{\frac{S \cdot D}{k \cdot L} + 1} \cdot e^{-t/\tau} + \frac{1}{1 + \frac{k \cdot L}{S \cdot D}}\right) \quad (6a)$$

Such a change in the heating power, in particular switching the heater on or off, can be implemented in very simple manner and can be caused to occur at a well-defined time. The sensor may also be switched on and off periodically in order to generate heating pulses. If the cycle of the heating pulses is in the order of the time constant τ, the phase lag between the heating pulse train and the measured signal will be indicative of the diffusion properties of the analyte.

Alternatively to repetitively switching the heater between full power and zero power, the heater may also be switched between non-zero, but different, power levels.

In more general terms, the invention can therefore also comprise the step of switching said heater from a first heating state to a second heating state, wherein said first and second heating states differ in heating power. In particular, the heating power of the first heating state can be zero. The heater should be kept in the first as well as the second heating state for at least a time in the order of time constant $\tau$. In view of the typical time constants described below, the heater should be kept in the first as well as the second heating state for at least a time of 0.05 seconds, in particular for at least 0.1 seconds.

For small values of the reaction rate k, the time constant $\tau$ is given by $(L \cdot V)/(S \cdot D)$, in other words it depends on the geometry (L, V and S) of passage 6 and on the diffusivity D of the analyte. Typical values of D for various gases in air at 300 K are e.g. (in $m^2/s$)

| | |
|---|---|
| $H_2O$ | $22 \times 10^{-6}$ |
| $CO_2$ | $14 \times 10^{-6}$ |
| CO | $19 \times 10^{-6}$ |
| ethanol | $11 \times 10^{-6}$ |

The following table shows typical values of $\tau$ (in seconds) for k=0, $D = 20 \times 10^{-6}$ $m^2/s$ for different values of L/S (in $mm^{-1}$) and V (in $mm^3$)

| L/S | V = 1 | V = 8 | V = 27 |
|---|---|---|---|
| 1 | 0.05 | 0.4 | 1.35 |
| 5 | 0.25 | 2 | 6.8 |

In other words, the time constant $\tau$ is typically in the order of 0.01 to 10 seconds for a cavity volume in the range of 1 to 30 $mm^3$ and a L/S ratio in the order of 1 to 5 $mm^{-1}$.

Experimental data is shown in FIG. 3 with a plot of the response of the sensor signal, which corresponds to the resistance of the device, when measuring ethanol in air at room temperature. At time 0, the concentration $c_{A0}$ of ethanol outside housing 10 was changed from 0% to 0.05%. For the measurement "without diffusion barrier" the sensor was directly connected to the surroundings, without a narrow passage 16, while in the measurement "with diffusion barrier" the sensor was arranged in a cavity that was connected via a passage with L=3 mm and a diameter of 0.8 mm (i.e. S=0.5 $mm^2$). The material of sensing layer 21 was Tin oxide.

As can be seen, the response of the set-up without diffusion channel is much faster than the response of the set-up with diffusion channel, i.e. with diffusion barrier.

Also, and as seen from a comparison of the two curves in FIG. 3, the steady-state response signal (i.e. the measured signal at a time $t \gg \tau$) is approximately twice smaller without diffusion barrier than with diffusion barrier. This is due to the fact that, in the diffusion-limited device, the equilibrium-case is characterized by the diffusion rate of ethylene through passage 16 being equal to the rate of catalytic decomposition of the ethylene at the MOX sensor. As it follows from Eq. (6)

$$c_{AV}(t = \infty) = \frac{c_{A0}}{1 + \frac{k \cdot L}{S \cdot D}}. \tag{7}$$

As can be seen, the concentration $c_{AV}$ within cavity 17 is smaller than the concentration $c_{A0}$ outside housing 10 as soon as catalytic decomposition takes place, i.e. when k>0. Since the sensor signal plotted in FIG. 3 corresponds to the resistance of the device and therefore decreases when concentration of ethanol increases, the value of the response is smaller without diffusion barrier than with diffusion barrier.

It must be noted that the diffusion model described above and in reference to FIG. 2 is only a rough approximation. A more refined model can be derived theoretically, or it can be derived experimentally by recording a sufficiently large number of responses and relaxations, e.g. of the type shown in FIG. 3, for a number of analytes.

In general, a model that predicts the time dependence of the concentration $c_{AV}(t)$ in cavity 17 will typically be a function of the type $$c_{AV}(t) = F(t, k, D, d, V, c_{A0}) \tag{8}$$

with k being a parameter indicative of the reaction rate of analyte A at the sensing layer, D the diffusivity of A, and d describing the geometry of the diffusion barrier (such as duct 16) and V being the volume of cavity 17. $c_{A0}$ is the unknown concentration of the analyte outside housing 10.

While the parameters d and V are independent of the type of analyte, the parameters k and D depend on the nature of the analyte.

Analyte Analysis:

Eq. (8) shows that the time dependence of the concentration $c_{AV}$ in cavity 17 (and therefore the signal measured by gas sensor 18) depends on the material parameters D and k, which in turn depend on the analyte to be measured.

By taking a sufficient number of measurements, advantageously more than two measurements, during a response to a change of the boundary conditions, i.e. while the concentration $c_{AV}$ is in a non-steady state, $c_{AV}(t)$ can be recorded as a function of time. The parameters $c_{A0}$, k and D of Eq. (8) can then be fitted, e.g. using a standard least-squares fitting algorithms, such that Eq. (8) describes the measurements. Therefrom, not only $c_{A0}$ can be calculated, but also at least one of the material parameters k and D, which allows to obtain information about the type of analyte that was measured. In this context, the process of fitting the material parameters k and D is to be understood as fitting any parameter that is indicative of k and/or D.

In a simplified scenario, and depending on the range of analytes that are to be measured, it is conceivable to assume that the diffusivity D is basically the same for all the analytes, e.g. $15 \times 10^{-6}$ $m^2/s$, in which case two measurements during the transient phase of the response suffice in order to determine the parameters k and $c_{A0}$, therefrom deriving the concentration as well as the type of the analyte.

Hence, in more general terms, the procedure described so far allows to determine the nature of the analyte by bringing the device into a mode of operation where the concentration $c_{AV}$ of the analyte within the cavity is in a non-steady state, and by taking at least two measurements while the concentration relaxes into the equilibrium state.

It must be noted that the non-steady state can be created in various ways. In the example described above, the non-steady state was created by changing the concentration $c_{A0}$ of the analyte outside the housing 10 at said passage, in particular in stepwise manner (i.e. in a time-frame much smaller than the time constant $\tau$) from zero to a non-zero value.

Figure 4:
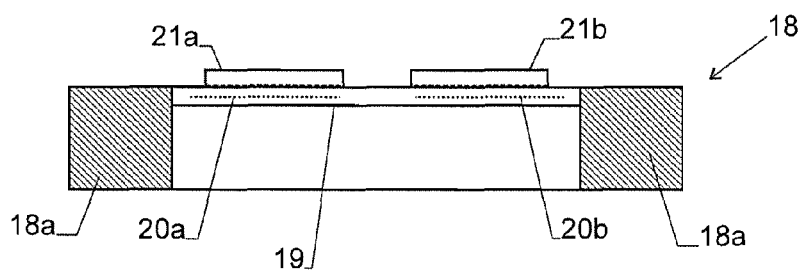
FIG. 4 is a sectional view of an alternative gas sensor.

Another way to generate the non-steady state is by changing the value of the reaction rate k. For example, if gas sensor 18 comprises two heaters 20a, 20b individually heating two sections or regions 21a and 21b of sensing layer 21, as shown in FIG. 4, the value of k can be doubled by switching on both heaters. Varying k in this way, i.e. by e.g. first switching on only one of the heaters during a first period of time and then switching on both heaters at time 0, or vice versa, leads to a non-steady state that will move back to a steady state under the regime of Eqs. (8) or (4).

In more general terms, the reaction rate can be changed by first heating a first region of the metal-oxide sensing layer and then heating a second region of the metal oxide sensing layer, with said first and said second region having different areas. The first and second region may or may not overlap. Advantageously, both regions are heated to the same temperature in order to obtain the same reactivity (=reaction rate per surface unit) in both cases.

Making measurements in both operating modes, i.e. when operating both or only one heater 20a, 20b, respectively, allows to obtain two sets of measured values described by two functions F of the type of eq. (8), which differ by their parameter k only, which allows to obtain more accurate estimates of the parameters by using standard curve fitting techniques.

Further, it must be noted that the value of $c_{AV}(t)$ is typically linearly dependent on $c_{A0}$, see e.g. Eq. (6), in which case Eq. (8) can be rewritten as $$c_{AV}(t) = c_{A0} \cdot F'(t,k,D,d,V) \qquad (9)$$

Hence, when a first measurement is carried out by heating only one of the heaters 20a, 20b (i.e. for a given value of reaction rate k), thereby measuring a time dependent $c_{AV1}(t)$, and then a second measurement is carried out, from the same starting conditions, by heating both heaters 20a, 20b (in which case the reaction rate is 2·k, thereby measuring a time dependent $c_{AV2}(t)$, and then dividing $c_{AV1}(t)$ by $c_{AV2}(t)$, one obtains $$c_{AV1}(t)/c_{AV2}(t) = F'(t,2k,D,G,V)/F'(t,k,D,G,V) \qquad (10)$$

Function F' is independent on the concentration $c_{A0}$ of the analyte outside housing 10, and it only varies with the material parameters k and D of the analyte. Hence, from $c_{AV1}(t)/c_{AV2}(t)$ it is possible to directly derive the type of analyte that is measured. For example, F' (t, 2k, D, d, V)/F' (t, k, D, d, V) can be recorded, for at least one time t, in a calibration measurement, for a plurality of different reference analytes, and then be stored in the sensor device as reference data. When measuring an unknown analyte, the best matching reference analyte can be determined from the stored reference data.

It must be noted that the ratio $c_{AV1}(t)/c_{AV2}(t)$ required for Eq. (10) can be determined by calculating the quotient of the measured raw signals (such as signals indicative of the conductance of the sensing layer) if the measured raw signals are at least roughly proportional to the concentration of the analyte. If that is not the case, the raw signals have to be linearized first, e.g. by using calibration data obtained in calibration measurements or by exploiting the fact that the conductance of the sensing layer is typically proportional to a power of the concentration of the analyte and can therefore be (at least roughly) linearized by taking its logarithm.

Albeit a higher accuracy can be achieved by measuring the values of $c_{AV1}(t)$ and $c_{AV2}(t)$ at a plurality of times, it must be noted that it is sufficient to measure the values of $c_{AV1}(t)$ and $c_{AV2}(t)$ at one single time only, e.g. at a time t>>τ (i.e. in equilibrium state) in order to obtain a unique material parameter independent of the concentration $c_{A0}$. For example, using the model of Eq. (4), one obtains $$c_{AV}(t \gg \tau) = \frac{c_{A0}}{1 + \frac{k \cdot L}{S \cdot D}} \qquad (11)$$

Therefore, when recording $c_{AV1}(t)$ for a reaction rate k and $c_{AV2}(t)$ for a reaction rate 2k, we obtain $$\frac{c_{AV1}(t \gg \tau)}{c_{AV2}(t \gg \tau)} = \frac{1 + \frac{2 \cdot k \cdot L}{S \cdot D}}{1 + \frac{k \cdot L}{S \cdot D}}, \qquad (12)$$

which yields a parameter that allows to distinguish between any analytes that differ in k and/or D.

Further, it must be noted that varying the area of the heated sensing layer 21 is not the only means for varying the reaction rate k. Another means for changing the reaction rate k is provided e.g. by changing the sensor's operation temperature. This can be realized e.g. by pulsing the electrical current through heater 20 by means of current pulses. A membrane-based gas sensor 18 as shown e.g. in FIGS. 2 and 4 allows to bring sensing layer 21 from room temperature to operating temperature (or back) within a time frame $\tau_{membrane}$ of a few milliseconds, i.e. within a time frame that is typically much smaller than the diffusion limited time scale τ. Hence, the average value of the reaction rate k can be varied by changing the duty cycle of the current pulses. For example, by doubling the length of the heating pulses while keeping their frequency f constant (with $\tau_{membrane}$<1/f<<τ), the reaction rate k can be doubled.

In more general terms, and similar to the slower pulse regime described above, the invention can therefore also comprise the step of switching said heater repetitively from a first heating state to a second heating state, wherein said first and second heating states differ in heating power. In particular, the heating power of the first heating state can be zero. The heater should be kept in the first as well as the second heating state for a time much smaller than time constant τ. In view of the typical time constants described above, the heater should advantageously be kept in the first as well as the second heating state for no more than 1 second, in particular for no more than 0.05 seconds, and/or for no less than 5 ms.

Hence, in a general manner, the present method for identifying an analyte from a set of analytes comprises the following steps:

1) A measurement device is provided. This device has
   a housing,
   a cavity within the housing,
   a metal-oxide gas sensor comprising a metal-oxide sensing layer and a heater for heating the sensing layer, and
   a passage extending between the cavity and the outside of the housing.
2) Heating the metal-oxide sensing layer, thereby generating a condition where said analyte diffuses into said cavity through said opening and is catalytically decomposed with a reaction rate k at said metal-oxide sensing layer;
3) Taking at least two measurements indicative of the electrical conductivity of said metal oxide sensing layer, wherein the measurements are taken a) during a phase where a concentration $c_{AV}$ of the analyte within the cavity is in a non-steady state (i.e. where the concentration $c_{AV}$ varies over time) and/or b) for different reaction rates k.

4) Deriving at least one material parameter indicative of the type of the analyte (such as the diffusivity D and/or the chemical reactivity at the MOX layer) from these measurements. From this material parameter, the type of analyte and/or a more accurate value of concentration $c_{A0}$ can be derived, e.g. by means of a look-up table.

Notes:

Passage 16 forms a throttle with the effect to reduce the diffusion of the analyte to the metal oxide sensing layer. In the shown embodiments, passage 16 is a tubular, open duct extending from the outside of housing 10 to cavity 17. Alternatively, a partially permeable diffusion barrier, such as a porous material, can be inserted in passage 16 in order to decrease the diffusion rate.

As can be seen from Eq. (5), the volume V of the cavity affects the time constant τ, but not the equilibrium value at t>>τ. Hence, if a measurement using above step 3a (i.e. a measurement during the non-steady state) is to be carried out, volume V should be sufficiently large such that τ exceeds the chemical response time of the metal oxide sensor. Assuming that k is comparatively small, if follows from Eq. (5) that $$\tau \cong \frac{L \cdot V}{S \cdot D} \quad (13)$$

(This assumption may not always be justified. For example, the data of FIG. 3 indicate that the factor 1+kL/(SD) of Eq. (7) is not equal 1, i.e. kL not much smaller than SD.)

In order to generalize over the simple diffusion model of FIG. 2, we assume that the diffusion rate R through passage 16 into cavity 17 is given by $$R = -d \cdot (c_{AV} - v_{A0}) \cdot D, \quad (14)$$

with d being a diffusion constant describing the diffusion through said passage and depending on the geometry and design of passage 16 (d=S/L for the model of FIG. 2). (For a given passage 16, d can be measured by setting $c_{AV}$ and $c_{A0}$ for a given analyte to known values and by measuring the diffusion rate R.)

Hence, when neglecting the contribution of the catalytic decomposition of the analyte, the time constant τ can be approximated by $$\tau \cong \frac{V}{d \cdot D}. \quad (15)$$

Assuming that D is in the order of $0.5 \ldots 30 \times 10^{-6}$ m$^2$/s for typical gaseous analytes in air at room temperature (e.g. $5 \times 10^{-6}$ m$^2$/s for octane and $28 \times 10^{-6}$ m$^2$/s for NH$_3$), and assuming that τ should be between 1 and 10 seconds if the time constant has to be determined within reasonable time, the ratio V/d should be 5 . . . 300 mm$^2$, in particular 10 . . . 100 mm$^2$. For example, in the simple model above, if passage L has a length of 3 mm and a diameter of 1 mm, d=S/L=0.26 mm and therefore V should be between 1.31 mm$^3$ and 78 mm$^3$, in particular between 2.6 mm$^3$ and 26 mm$^3$. As can be noted, these values of V are fairly large for a compact device, i.e. it can be advantageous to use a passage 16 where S/L is smaller than 0.26 mm.

On the other hand, if a quick response is desired, e.g. when using step 3b) of the method above, τ should be less than 10 seconds, in particular less than 1 second. In that case, for an analyte with a diffusivity at the lower end, i.e. at $5 \times 10^{-6}$ m$^2$/s, V/d should be less than 50 mm$^2$, in particular less than 5 mm$^2$.

As mentioned above, the present technology allows to identify the analyte that is measured by the sensing device. Once this analyte is known, the material properties k and D are known as well. Therefore, a more accurate measurement of the concentration $c_{A0}$ becomes possible, e.g. using Eq. (4), (8) or (11).

The steps of the present method can be implemented in hard-, firm- or software within control unit 24.

The sensor device is, as shown in FIG. 1, advantageously a mobile phone, a tablet device or a portable computer.

The invention claimed is:

1. A method for determining a type and/or concentration of an analyte from a set of analytes comprising the steps of providing a measurement device having
   a housing,
   a cavity within said housing,
   a gas sensor comprising a metal-oxide sensing layer and a heater for heating the sensing layer, and
   a passage extending between the cavity and the outside of the housing,
heating the metal-oxide sensing layer, thereby generating a condition where said analyte is catalytically decomposed with a reaction rate k at said metal-oxide sensing layer,
taking at least two measurements on said metal oxide sensing layer indicative of a concentration of said analyte, wherein the measurements are taken
   during a phase where a concentration $c_{AV}$ of the analyte within the cavity is in a non-steady state,
deriving at least one material parameter indicative of the analyte from said measurements, using the diffusion kinetics of the analyte through the passage and using the catalytic decomposition kinetics of the analyte at said metal-oxide sensing layer,
wherein said at least two measurements are taken at different times during a phase where a concentration $c_{AV}$ of the electrolyte within the cavity is in a non-steady state and while the concentration $c_{AV}$ relaxes into an equilibrium state,
wherein a ratio V/d is between 5 and 300 mm$^2$, wherein
   V is a volume of said cavity and
   d is a diffusion constant depending on a geometry and design of said passage and describing the diffusion through said passage, with d being defined by $$R = -d \cdot (cAV - c_{A0}) \cdot D,$$

with R being a rate of diffusion of an analyte of diffusivity D, $c_{AV}$ is a gas concentration in said cavity and $c_{A0}$ is a gas concentration outside said housing at said passage,
wherein said at least two measurements are taken for different reaction rates k,
further comprising a step of changing said reaction rate by heating a first region of the metal-oxide sensing layer and then heating a second region of the metal oxide sensing layer, with said first and said second region having different areas, and in particular wherein said first and said second regions are heated to the same temperature.

2. A method for determining a type and/or concentration of an analyte from a set of analytes comprising the steps of
  providing a measurement device having
    a housing,
    a cavity within said housing,
    a gas sensor comprising a metal-oxide sensing layer and a heater for heating the sensing layer, and
    a passage extending between the cavity and the outside of the housing,
  heating the metal-oxide sensing layer, thereby generating a condition where said analyte is catalytically decomposed with a reaction rate k at said metal-oxide sensing layer,
  taking at least two measurements on said metal oxide sensing layer indicative of a concentration of said analyte, wherein the measurements are taken
    for different reaction rates k,
  wherein the method comprises further steps of
  changing said reaction rate by heating a first region of the metal oxide sensing layer and then heating a second region of the metal oxide sensing layer, with said first region and said second region having different areas, and
  deriving at least one material parameter indicative of the analyte from said measurements.

3. The method of claim 2, wherein said first region and said second region are heated to the same temperature.

\* \* \* \* \*